(12) United States Patent
Neatrour et al.

(10) Patent No.: US 9,457,135 B2
(45) Date of Patent: Oct. 4, 2016

(54) SUCTION CANISTER HAVING A REPLACEABLE FILTER CARTRIDGE

(71) Applicant: DeVilbiss Healthcare LLC, Somerset, PA (US)

(72) Inventors: Joel David Neatrour, Johnstown, PA (US); Matt Smith, Berlin, PA (US)

(73) Assignee: DeVilbiss Healthcare LLC, Somerset, PA (US)

( * ) Notice: Subject to any disclaimer, the term of this patent is extended or adjusted under 35 U.S.C. 154(b) by 702 days.

(21) Appl. No.: 13/692,041

(22) Filed: Dec. 3, 2012

(65) Prior Publication Data

US 2014/0155847 A1    Jun. 5, 2014

(51) Int. Cl.
*A61M 1/00*   (2006.01)
*B01D 35/027* (2006.01)
*B65D 43/02*  (2006.01)
*B65D 47/04*  (2006.01)

(52) U.S. Cl.
CPC ........... *A61M 1/0001* (2013.01); *A61M 1/005* (2014.02); *A61M 1/0052* (2014.02); *A61M 1/0056* (2013.01); *B01D 35/027* (2013.01); *B65D 43/02* (2013.01); *B65D 47/04* (2013.01); *A61M 2205/16* (2013.01); *B01D 2201/16* (2013.01)

(58) Field of Classification Search
CPC .... A61M 1/00; A61M 1/0001; A61M 1/005; A61M 1/0052; A61M 1/0056; A61M 2205/16; B01D 29/014; B01D 29/035; B01D 29/0029; B01D 29/071; B01D 29/0097; B01D 35/02; B01D 35/027; B01D 35/0276; B01D 35/157; B01D 35/1573; B01D 2201/16; B01D 2201/167; B01D 2201/30; B01D 2201/301; B08B 3/10; B08B 9/08; B08B 9/0804; B65D 5/00; B65D 5/02; B65D 5/18; B65D 5/28; B65D 43/00; B65D 43/02; B65D 47/00; B65D 47/04; A61C 17/04; A61C 17/046; A61C 17/14; B65B 7/28

USPC ....... 210/437, 439, 441, 446, 445, 457, 464, 210/470, 473, 416.1, 97; 604/319, 320, 604/405, 406

See application file for complete search history.

(56) References Cited

U.S. PATENT DOCUMENTS

| | | | |
|---|---|---|---|
| 3,286,446 A * | 11/1966 | Happe | ................... A47L 7/0095 15/327.5 |
| 3,612,089 A * | 10/1971 | Beguiristain | ............ 137/115.02 |
| 3,814,098 A * | 6/1974 | Deaton | ............... A61M 1/0001 604/320 |
| RE29,321 E | 7/1977 | Holbrook | |
| 4,228,798 A * | 10/1980 | Deaton | ........................ 604/540 |
| 4,487,606 A | 12/1984 | Leviton et al. | |
| 4,561,868 A * | 12/1985 | von Reis et al. | ............... 55/319 |
| 4,870,975 A * | 10/1989 | Cronk et al. | .................. 600/562 |
| 5,470,324 A | 11/1995 | Cook et al. | |
| 5,792,126 A | 8/1998 | Tribastone et al. | |
| 6,652,495 B1 | 11/2003 | Walker | |
| 7,357,142 B2 | 4/2008 | Merkle | |
| 7,806,879 B2 | 10/2010 | Brooks et al. | |
| 8,062,273 B2 | 11/2011 | Weston | |
| 8,257,328 B2 | 9/2012 | Augustine et al. | |
| 2003/0178360 A1* | 9/2003 | Haldopoulos et al. | ........ 210/435 |
| 2004/0255783 A1* | 12/2004 | Graham | .................. A47L 9/122 96/69 |
| 2008/0281283 A1 | 11/2008 | Walker | |

(Continued)

*Primary Examiner* — Joseph Drodge
(74) *Attorney, Agent, or Firm* — Bryan Cave LLP

(57) ABSTRACT

A canister assembly for use with a medical suction or aspiration device having a ball float assembly defined in the lid. The lid accepts a replaceable filter cartridge containing a filter element. The ball float engages the replaceable filter cartridge when the canister is near full.

12 Claims, 6 Drawing Sheets

(56) References Cited

U.S. PATENT DOCUMENTS

2009/0012485 A1* 1/2009 Michaels ............ A61M 1/0001 604/320

2012/0046624 A1* 2/2012 Locke ................ A61M 1/0001 604/319

2012/0215187 A1* 8/2012 Tippet ................ A61M 1/0001 604/319

* cited by examiner

SUCTION CANISTER HAVING A REPLACEABLE FILTER CARTRIDGE

FIELD OF THE INVENTION

This invention relates in general to canisters. More specifically, the invention is directed to canisters for use with a medical suction or aspirator device for the collection of fluids during medical procedures.

BACKGROUND OF THE INVENTION

Medical suction and aspiration devices are used to remove bodily fluids during medical procedures or emergency situations. These suction and aspiration devices often include canisters to receive the bodily fluids. Current devices used for aspiration during surgical procedures include a wandlike collection device connected via a hose to a collection canister. A vacuum pump is also connected to the canister, thereby creating a vacuum in the canister and in the collection device. As aspirated fluids are removed from the body, they are collected in the collection canister.

As it is desirable to minimize contact between the suctioned fluid within the canister and the device operator, and to avoid having fluids sucked into the vacuum pump, it is desirable to provide a means for the isolating the fluids from the orifice to which the vacuum source is connected.

BRIEF SUMMARY OF THE INVENTION

This invention relates to a canister having a filtered, shut off device to retain suctioned fluids within the canister. The device consists of a ball float valve which is capable of making contact with a replaceable filter cartridge. An absorbent valve which constricts the flow of air and fluids when wet, is disposed within the filter cartridge to prevent fluid flow through the vacuum source. In operation, when the canister becomes full, the ball float will rise, blocking the bottom inlet to the filter cartridge. Any fluids that may leak past the ball float will contact the absorbent valve, which will ensure that no fluids are able to enter the vacuum source.

DESCRIPTION OF THE INVENTION

Figure 1:
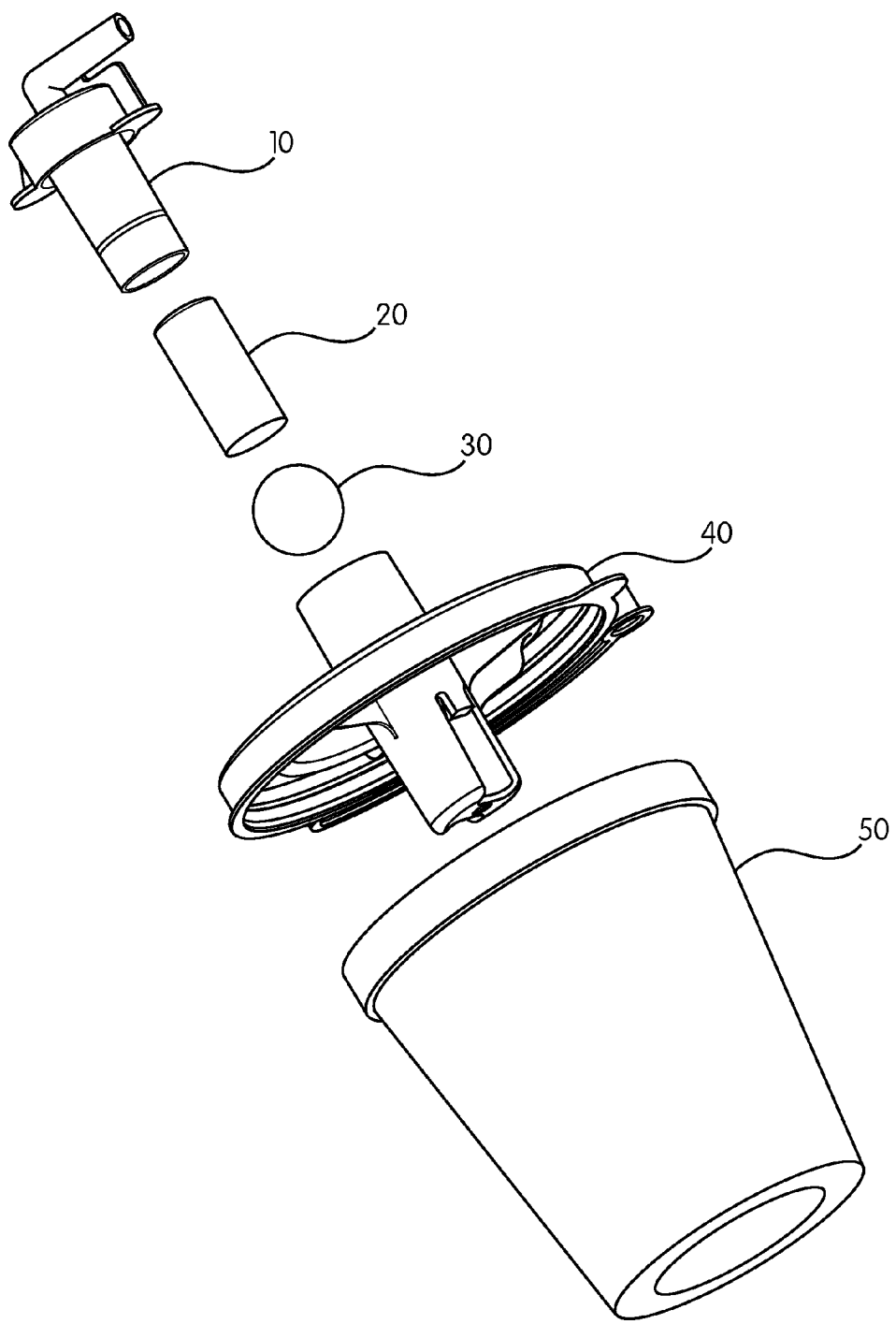
FIG. 1 shows the device in transparent perspective exploded view.

FIG. 1 shows an exploded view of the device of the present invention. When in use, canister 50 is used to collect aspirated bodily fluids. In practice, after use, canister 50 is often emptied and cleaned for re-use, as is lid 40. Canister 50 may be composed of styrene acrylonitrile or another hard plastic. Lid 40 uses replaceable filter cartridge 10, which may be replaced between uses of the device. The novelty of the invention is in the design of lid 40, and filter cartridge 10 to allow the replacement of filter cartridge 10 for re-use. Note that lid 40 and filter cartridge 10 wherein the novel aspects of the invention reside, may be used with canister bodies 50 of many different types. Lid 40 contains the housing for the ball float valve as well as the inlet port to which the suction wand is typically connected. Ball float 30 rests inside lid 40, as will be explained later. Replaceable filter cartridge 10 retains filter element 20 therein and also includes the orifice for connection to the vacuum source.

Figure 2:
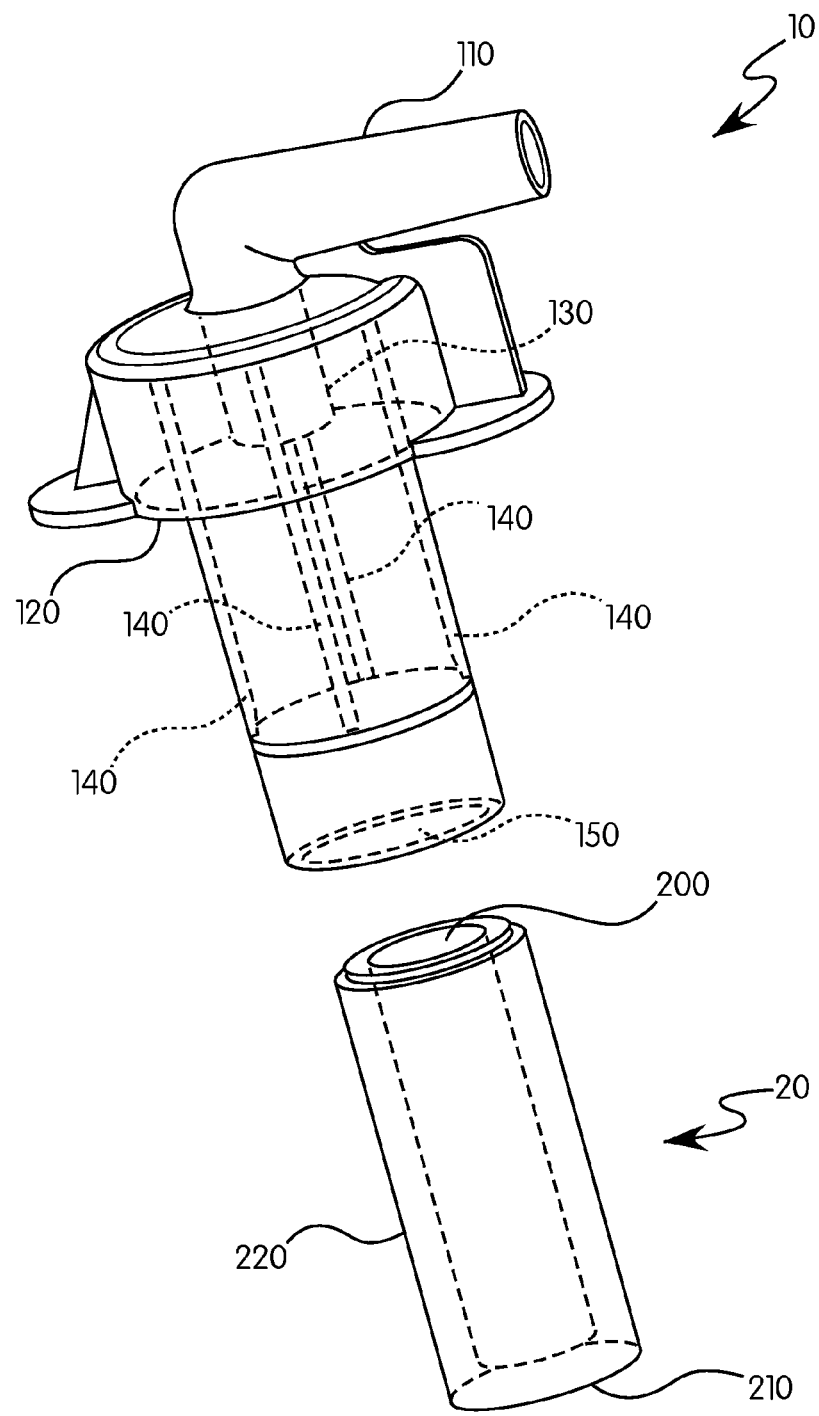
FIG. 2 shows the filter cartridge and filter element in perspective transparent view.

FIG. 2 shows the filter cartridge in transparent perspective view. Preferably, filter cartridge 10 is composed of a low density polyethylene As can be seen, filter element 20 consists of a hollow cylinder 220 closed at one end 210 and being open at the other end. Opening 200 opens to a cylindrical void inside filter element 20. Filter element 20 slides into the body of filter cartridge 10, engaging nipple 130 in opening 200 and is held in place by a plurality of ridges 140 defined along the inner surface of cylindrical portion of filter cartridge 10. Nipple 130 is in fluid communication with orifice 110 for connection to vacuum source. In operation, a vacuum is created by extracting air through orifice 110 and thereby through the void 200 in filter element 20. Air is able to flow in through the walls 220 of filter element 20 as long as filter element 20 has not become wet, thereby creating a negative pressure condition within canister 50.

Figure 6:
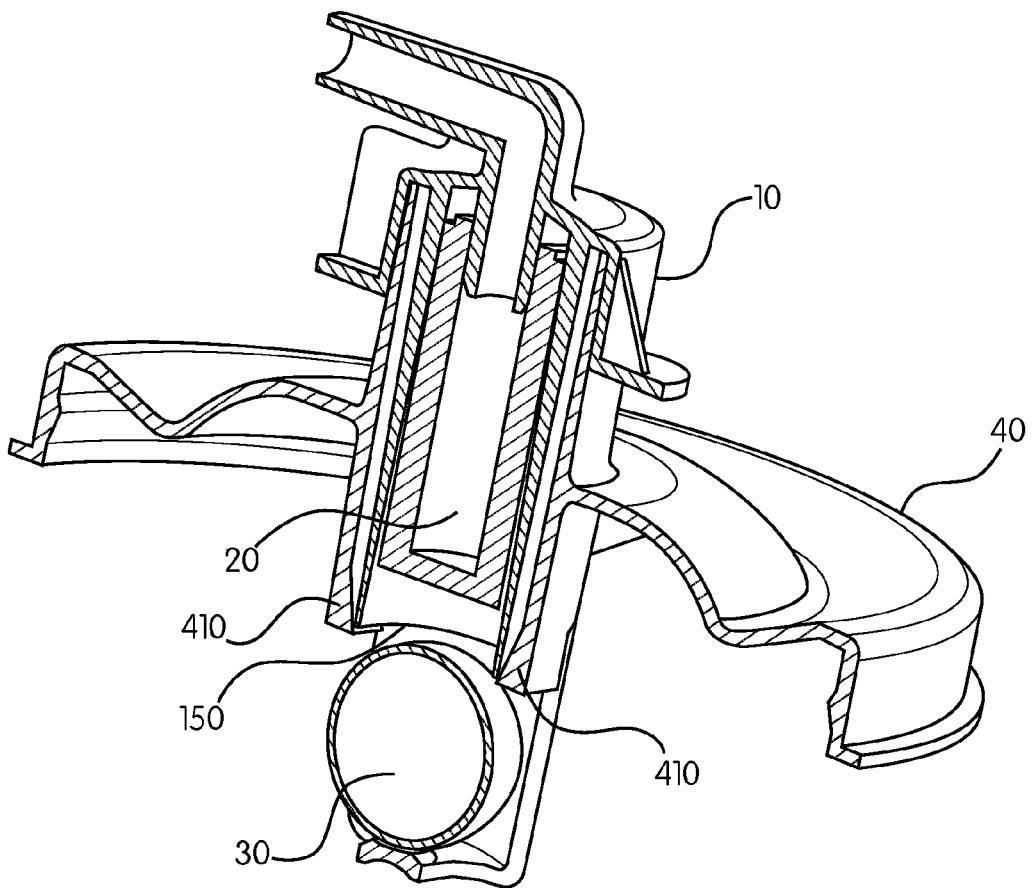
FIG. 6 shows the lid of the device having the filter cartridge inserted therein, in transparent, cross sectional view.

Lip 120 define on filter cartridge 10 engages in opening 430 defined in lid 40 and is held in place thereon by frictional engagement. FIG. 6 shows a cross-sectional view or lid 40 having filter cartridge 10 inserted therein. Opening 150 defined in the bottom of filter cartridge 10 is shaped and sized to engage the outer surface of ball float 30 when ball float 30 has floated up and is in contact with the bottom of filter cartridge 10. Preferably, the lower portion of the outer wall of filter cartridge 10 is slightly flexible.

Figure 3:
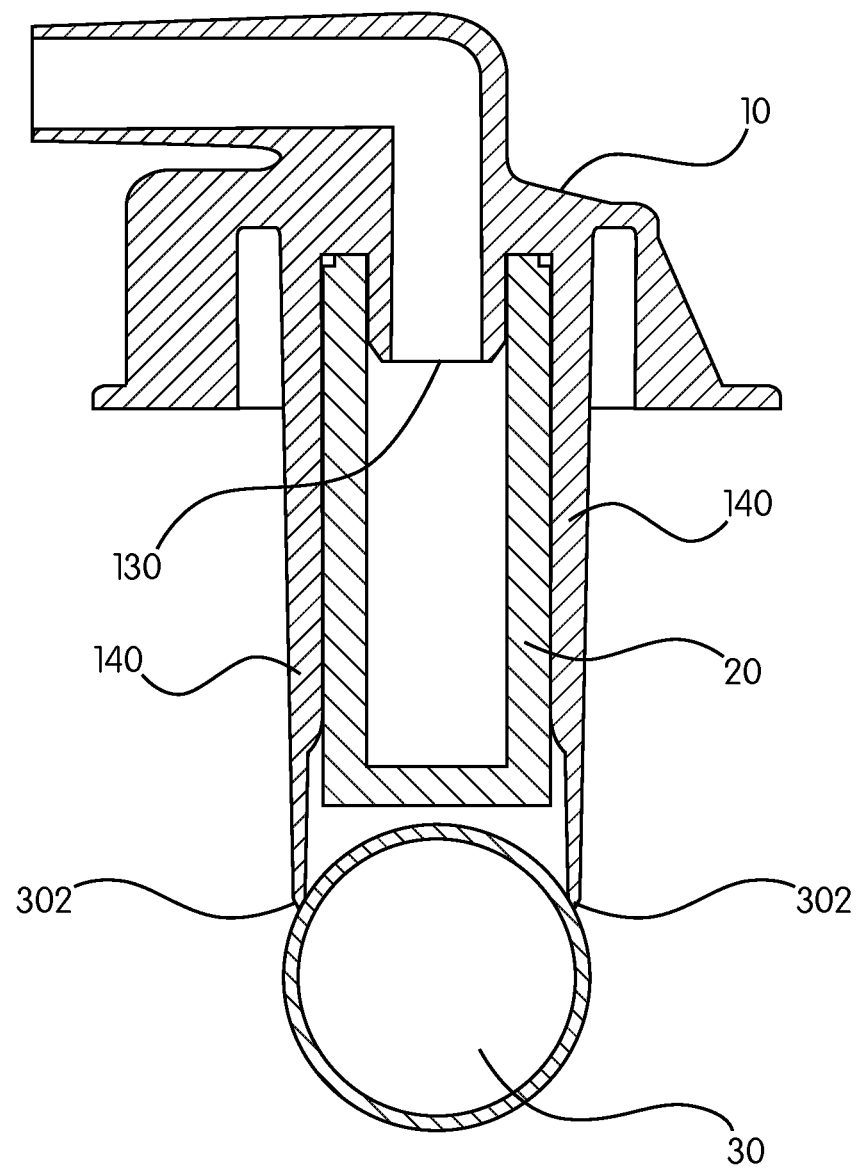
FIG. 3 shows the filter cartridge in cross-sectional view showing the ball float in position to stop the flow of fluid into filter cartridge 10.

FIG. 3 shows a cross-sectional view of filter cartridge 10 having filter element 20 inserted therein and also shows ball float 30 in contact with the bottom opening 150 of filter cartridge 10. Ball float 30 would be in this position in the event that canister 50 becomes filled with fluid, thereby causing ball float 30 to float up from its resting position to contact the bottom opening 150 of filter cartridge 10.

Figure 4:
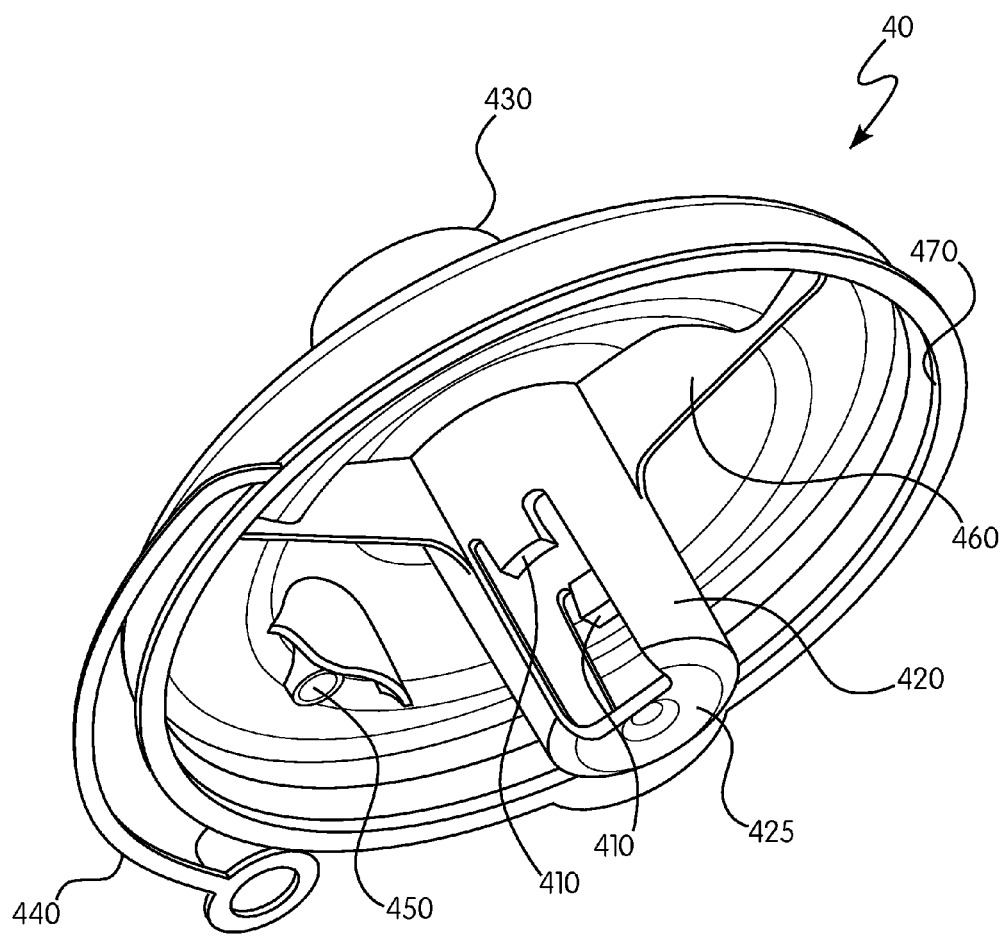
FIG. 4 shows a transparent perspective view of the bottom of the lid of the device.

FIG. 4 shows a perspective transparent view of the bottom of lid 40 of the device. Lid 40 defines receptacle 420 which holds ball float 30 and which received filter cartridge 20. Ball float 30 held with in receptacle 420 by retaining tabs 410 which can be flexed outwardly such as to allow the removal of ball float 30 from receptacle 420 for cleaning purposes. However, under normal circumstances, ball float 30 is unable to move past retaining tabs 410. Preferably, lid 40 is composed of a high density polyethylene and ball float 30 is composed of polypropylene, and may be hollow.

The distance between the bottom of retaining tabs 410 and the bottom wall 425 of receptacle 420 is sized to be greater than the diameter of ball float 30. In normal operation, ball float 30 will rest against bottom wall 425 of receptacle 420 and, in situations where canister 50 has become filled with fluid, ball float 30 will float up until further movement is prevented by bottom opening 150 of filter cartridge 10. Filter cartridge extends downward into receptacle 420, such that bottom opening 150 of filter cartridge 10 is even with retaining tabs 410, as shown in FIG. 6. Thus, when ball float 30 has floated up and is in contact with retaining tabs 410, opening 150 of filter cartridge 10 will also be blocked by ball float 30. The width of receptacle 420 is slightly larger than the diameter of ball 30, allowing vertical movement of ball float 30 within receptacle 420.

Also shown in FIG. 4 are other design elements of lid 40 including structural ridges 460, inner lip 470 which engages the upper lip of canister 50, in this case utilizing a snap fit, although other means of engagement may also be used. Also shown is inlet port 450 which connects on the upper surface of lid 40 (not shown) with the collection device, typically an aspirator. Cap 440 may be used to close inlet port 450 from the outside when no collection device is connected thereto. Lid 40 defines opening 430 on the top thereof for reception of the filter cartridge 10 having filter element 20 inserted therein.

Figure 5:
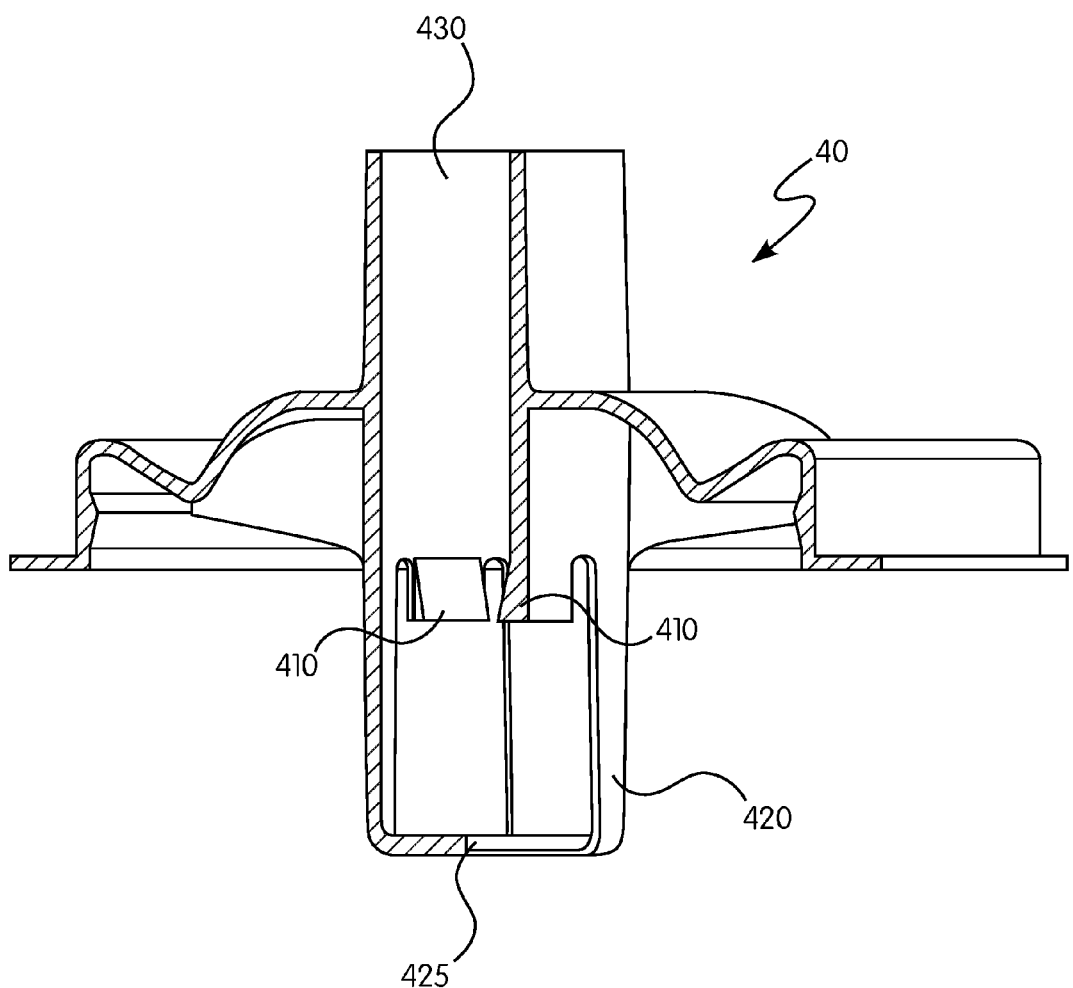
FIG. 5 shows the lid of the device in transparent cross-sectional view.

FIG. 5 is a cross-sectional transparent view of lid 40 showing in more detail receptacle 420 in which ball float 30 is disposed and the size and spacing of retaining tabs 410, which keep ball float 30 in place during normal operation of the device. Filter cartridge 10 is inserted into opening 430 defined in the top of lid 40. The ridge of bottom opening 150 of filter cartridge 10 extends to the bottom level of retaining tabs 410, such that when ball float 30 has floated upward, a portion of ball float 30 will extend above retaining tabs 410 to close the bottom of filter cartridge 10, as shown in FIG. 3.

As in many instances, canister 50 and lid 40 are reused by medical personnel. It is intended that filter cartridge 10 along with filter element 20 inserted therein be replaceable and sold separately from the rest of the device such that lid 40 and canister 50 may be reused many times. It is also intended that ball float 30 be easily removed from receptacle 420 by forcing it past retaining tabs 410, which are flexible enough to allow the passage of ball float 30 upwards through opening 430 when pressure is applied from the bottom of ball float 30.

Filter element 20 includes an open end 200, which engages nipple 130 on the interior of filter cartridge 10, an outer wall 220, and a closed end 210. The outer wall 220 and the closed end 210 have an interior surface, an exterior surface, and cooperate to define an interior space, cylindrically-shaped space. The material of the absorbent valve 34 may be of a porous structure having interstitial voids, such as between sintered beads or intertwined filaments, thus creating a capillary effect therein.

Filter element 20 is preferably made from a material exhibiting a hydrophilic or hygroscopic property. This fluid absorptive property of filter element 20 is aided, at least in part, by the capillary action of the interstitial voids of the material. The structure can be made from sintering plastic beads or powders. Such a structure may be formed by a polyethylene plastic having an added cellulose gum filler. Additionally, any suitable plastic or polymer capable of having a porous structure may be a suitable material substitute to support a cellulose gum filler. The cellulose gum filler is used as the reactant medium to reduce the interstitial voids, thus slowing and ceasing fluid flow therethrough. Upon contact with fluid, the interstitial voids of the material of the outer wall 220 and the closed end 210 gradually reduce to increasingly restrict air and fluid permeability, thus preventing bodily fluid fro entering the vacuum source through orifice 110.

While the invention has been described with reference to particular embodiments, it should be understood that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiments, but that the invention shall include all embodiments falling within the scope of the following claims.

We claim:

1. A lid assembly for a suction canister comprising:
   a lid body, having a lip defined therein for engagement with a canister;
   a hollow cylindrical structure, having a top portion extending above a top surface of said lid and having an open top end, and a bottom portion extending below a bottom surface of said lid, and having an open bottom end;
   a bottom wall, covering all or a portion of said open bottom end of said bottom portion of said hollow cylindrical structure;
   one or more openings, defined in the bottom portion of said cylindrical structure;
   one or more tabs, defined in said bottom portion of said cylindrical structure, said tabs extending into an interior of said cylindrical structure;
   a ball float, disposed on the interior of said hollow cylindrical structure between said bottom wall and said one or more tabs, such that said ball float can move within the interior of said hollow cylindrical structure between said bottom wall and said one or more tabs.

2. The lid assembly of claim 1 wherein said lid body defines an orifice therein.

3. The lid assembly of claim 1 wherein all elements of said lid assembly comprise polyethylene.

4. The lid assembly of claim 1 wherein said ball float comprises polypropylene.

5. The lid assembly of claim 1 further comprising:
   a filter cartridge, disposed in said cylindrical structure.

6. The lid assembly of claim 5 wherein said filter cartridge comprises:
   a cylindrical body having a first diameter smaller than the diameter of the top portion of said hollow cylindrical structure;
   a cap having a second diameter larger than the diameter of the top portion of said hollow cylindrical structure; and
   a tube, extending through said cap, allowing fluid communication between an interior of said filter cartridge and the exterior of said filter cartridge.

7. The lid assembly of claim 6 wherein said cylindrical body and said cap form a space therebetween for acceptance of said open top end of said cylindrical structure.

8. The lid assembly of claim 7 wherein said filter cartridge is held in the top portion of said hollow cylindrical structure by a friction fit.

9. The lid assembly of claim 7 where the cross-sectional diameter of said cylindrical body is less than the diameter of said ball float.

10. The lid assembly of claim 6 wherein said filter cartridge comprises polyethylene.

11. The lid assembly of claim 6 further comprising a filter element, disposed in said cylindrical body, said filter element engaging said tube.

12. The lid assembly of claim 11 wherein said filter element comprises a material exhibiting hydrophilic or hygroscopic properties.

* * * * *